United States Patent
Viscomi et al.

(10) Patent No.: US 6,960,341 B2
(45) Date of Patent: Nov. 1, 2005

(54) BIFIDOBACTERIA AND PREPARATIONS CONTAINING THEM

(75) Inventors: Claudio Giuseppe Viscomi, Sasso Marconi (IT); Leone Gabriele Rotini, Bologna (IT); Lorenzo Morelli, Piacenza (IT); Patrizio Ferrari, Bologna (IT); Maria Rosaria Pantaleo, Bologna (IT)

(73) Assignee: Alfa Wassermann S.p.A., Alanno Scalo (Pescara) (IT)

( * ) Notice: Subject to any disclaimer, the term of this patent is extended or adjusted under 35 U.S.C. 154(b) by 86 days.

(21) Appl. No.: 10/621,296

(22) Filed: Jul. 17, 2003

(65) Prior Publication Data

US 2004/0047850 A1 Mar. 11, 2004

(30) Foreign Application Priority Data

Sep. 6, 2002 (IT) .................................. BO2002A0564

(51) Int. Cl.⁷ .................. A01N 63/00; A01N 65/00; C12N 1/00; C12N 1/12
(52) U.S. Cl. .................. 424/93.4; 424/93.1; 435/252.1; 435/822
(58) Field of Search .............. 424/93.4, 93.1; 435/252.1, 822, 243

(56) References Cited

U.S. PATENT DOCUMENTS

| | | | |
|---|---|---|---|
| 5,494,664 A | 2/1996 | Brassart et al. | |
| 6,241,983 B1 | 6/2001 | Paul et al. | |
| 6,783,780 B1 * | 8/2004 | De Jong et al. | .............. 426/52 |

FOREIGN PATENT DOCUMENTS

| WO | WO 00/33854 | | 12/1999 |
|---|---|---|---|
| WO | WO 01/10453 | A2 | 7/2000 |

* cited by examiner

*Primary Examiner*—David M. Naff
*Assistant Examiner*—Deborah K. Ware
(74) *Attorney, Agent, or Firm*—Bucknam and Archer

(57) ABSTRACT

The disclosure refers to biologically pure cultures of two strains of *Bifidobacterium Longum* named W11 and W11a and deposited at the Belgian Coordinated Collections of Microorganisms (BCCM) that has registered them under the accession numbers LMG P-21586 and LMG P-21587. They are used as probiotics within preparations of pharmaceutical or alimentary products to help the gastrointestinal health and to prevent and treat the intestinal pathologies.

14 Claims, No Drawings

BIFIDOBACTERIA AND PREPARATIONS CONTAINING THEM

BACKGROUND OF THE INVENTION

The present invention refers to the use of non-pathogenic microorganisms of the genus *Bifidobacterium Longum* in order to help the gastrointestinal health and in particular in order to prevent and/or treat the indispositions of the gastrointestinal tract, particularly of the intestine.

Many types of bacteria used as fermenting agents for preserving foods or preparing from milk foods like yogurt or other dairy products are known since a lot of time; these bacteria are called under the general term of "lactic acid bacteria" and comprise many genera like *Lactococcus, Lactobacillus, Streptococcus, Bifidobacterium e Pediococcus*.

More recently, these bacteria are become object of greater attention because, when swallowed, they have shown remarkable properties on man and animals; in particular strains of *Lactobacillus* or *Bifidobacterium*, sometimes administered together in combination, have shown efficacy in colonizing the intestinal mucosa and in helping the health of the people, by preventing the colonization from other harmful microorganisms, as quoted in U.S. Pat. Nos. 5,494,664 and 6,241,983 and in International patent applications WO 0033854 and WO 0110453.

These microorganisms are also called "probiotics" and a fundamental requisite for their beneficial effect is that they can reach the intestinal mucosa in a such number and with a such vitality that they are able to persist and to colonize the intestine, therefore it is necessary they suitably resist the low pH of the stomach.

The assumption of probiotic products is recommended in case of intestinal indispositions, like constipation or diarrhoea and after periods of treatment with antibiotics, i.e. in particular in all those circumstances that bring to an impoverishment of the intestinal bacterial flora and also in all those circumstances when a feeding poor in fibres, environment conditions, or stress lower the vitality of the intestinal bacterial flora.

To restore suitable levels of microorganisms naturally present in the human bacterial flora by using bacterial strains well characterized and extracted from the flora of healthy people is the target of a such administration.

The colonizing activity of exogenous microorganisms in the intestine depends on their concentration, on their capability to colonize and on the environment conditions they find in the intestine, because the administration of a greater amount, a high capability of colonization and suitable environment conditions help its protective and curative effect through the colonization of great portions within the intestine without side effects as they are products of natural origin. In particular, it has to be underlined that the possible presence of alimentary fibres, like for instance inuline or fructo-oligosaccharides, mainly helps the colonization because these compounds are a substrate for the probiotic and therefore they increase the chances of colonization. Said oligosaccharides have also been called "prebiotics" because of this synergical action with the probiotic.

DESCRIPTION OF THE INVENTION

Biologically pure cultures of two strains of *Bifidobacterium Longum* called W11 and W11a deposited at the Belgian Coordinated Collections of Microorganisms—BCCM LMG-Collection that has registered them under the accession numbers LMG P-21586 and LMG P-21587, their use as probiotics within preparations of pharmaceutical or alimentary type and the preparations of pharmaceutical or alimentary type containing them useful to help the gastrointestinal health and to prevent and treat the intestinal pathologies are the object of the present invention.

The two strains of *Bifidobacterium Longum* W11 and W11a have been isolated from the intestinal bacterial flora of an healthy man and have been selected among many other strains of *Bifidobacterium Longum* contemporaneously isolated because they have shown a colonizing capability on the intestinal bacterial flora and a capability of adherence to the intestinal cells, characteristics that both make them very good probiotic agents able to help the good health of the gastrointestinal tract and to restore its altered functionality from gastroenteritis of various origin.

The bacterial cultures object of the present invention have been produced first in laboratory and then in industrial preparations and are made of pure strains that have been grown for 20 hours at 37° C. in a suitable culture medium called TPY containing as main ingredients tryptic casein peptone, soy-bean peptone, yeast extract and glucose in addition to potassium, calcium, magnesium and zinc salts.

From these primary cultures subsequent sub-cultures have been prepared with the aim to increase the number of cells of pure strains till to obtain the mother cultures that have been used as inoculation for the industrial production of the bacterial cultures of the two probiotics *Bifidobacterium Longum* W11 and W11a.

The industrial production process of said bacterial cultures provides for the following steps:

1. fermentation at a pH controlled between 5.5 and 7.5;
2. separation of the bacterial biomass from the culture broth by centrifugation;
3. lyophilization of the bacterial biomass, after addition of suitable cryoprotectors selected from proteids, carbohydrates and mineral salts to safeguard the cells vitality along the step of freezing and lyophilizing, possibly also with the addition of a proteic precipitate with the scope of increasing the resistance of the strain to the enzymatic degradation and to conditions of acidic pH;
4. milling and granulation of the lyophilized culture.

The so prepared product contains an average from about $1 \times 10^{10}$ to about $1 \times 10^{12}$ alive cells of *Bifidobacterium Longum* W11 or W11a for each gram of end product, analyzed according to microbiological methods of bacterial count known to a man skilled in the art, like for instance those reported in Ison A. P. and Matthew G. B., Applied Microbial Physiology a practical approach, Rhodes P. M. and Stanbury P. F. Editors—IRL Press Oxford, 103–130, 1997.

The bacterial cultures have been checked in colonization tests of the intestine of mice with positive results as the count of the amount of bacterial charge of *Bifidobacterium Longum* LMG P-21586 or LMG P-21587 has shown a value higher than $1 \times 10^6$ alive cells for each gram of faeces of mouse.

Further object of the present invention, strictly coming from the main object, is the use of the biologically pure cultures obtained from the strains of *Bifidobacterium Longum* W11 or W11a as probiotics in preparations of pharmaceutical or alimentary type useful in helping the gastrointestinal health and in preventing and treating the intestinal pathologies like diarrhoeas, gastroenteritis of various origin, constipation, irritable bowel, diverticular illness and chronic inflammatory diseases of the intestine.

The efficacy of the bacterial cultures containing the *Bifidobacterium Longum* W11 or W11a in helping the gastrointestinal health can be increased by adding to the preparations of pharmaceutical or alimentary type containing them alimentary fibres in the form of indigestible oligosaccharides, for instance fructo-oligosaccharides or inuline, that are not absorbed nor hydrolyzed in the first tract of the intestine and strengthen the activity and stimulate the metabolism of the strains of *Bifidobacterium Longum* LMG P-21586 and LMG P-21587 to disadvantage of the pathogenic bacteria. The oligosaccharides preferred in carrying out the present invention are admixtures of fructo-oligosaccharides made of a basic unit consisting in a glucose molecule (G) bound to a chain of fructose molecules (F) of general formula GFn, with $n \leq 4$, having a polymerization degree, i.e. a number of monosaccharidic units, between 2 and 20. The fructo-oligosaccharides used as prebiotics associated with the two types of probiotics object of the present invention have a polymerization degree between 2 and 10, preferably between 3 and 6.

The preparations object of the present invention can contain, together with various excipients like sweeteners, for instance aspartame, mannitol or sorbitol, flavouring and colouring substances, vitamins, preferably vitamins of the E, B1, B2, B6 and B12 groups, having the scope to further help the health by restoring the vitaminic component that undergoes a strong decrease during the pathologies of the intestinal tract.

Object of the present invention are both pharmaceutical preparations and alimentary products containing bacterial cultures of *Bifidobacterium Longum* called W11 and W11a and registered with the accession numbers LMG P-21586 or LMG P-21587, optionally in association with prebiotics, preferably fructo-oligosaccharides or inuline, and/or vitamins, preferably vitamins of the E, B1, B2, B6 and B12 groups.

The pharmaceutical preparations are preferably made of compositions administrable by oral route in form of capsules, tablets, packets, troches, liquid suspensions, dry oral supplements, liquid oral supplements, vials and some more containing a bacterial charge of alive cells of *Bifidobacterium Longum* W11 or W11a between $1 \times 10^7$ and $1 \times 10^{11}$ at the end of the stability period.

Said pharmaceutical preparations can also contain prebiotic agents like the fructo-oligosaccharides or the inuline, preferably from 0.5 to 5 g of fructo-oligosaccharide for each dose, more preferably from 1 to 3 g, and/or vitamins, preferably vitamins of the E, B1, B2, B6 and B12 groups.

Amounts of probiotic from $1 \times 10^7$ to $1 \times 10^{11}$ of alive cells of *Bifidobacterium Longum* can be incorporated also in the manufacture of many kinds of alimentary products like milk, yogurt, fresh cheeses like ricotta, stracchino and mozzarella (kinds of Italian cheese), ice-creams, products made of fermented milk, products made of fermented cereals, milk powders, children's products and products for domestic animals.

The tests for the check of the bacterial count have shown as both the strains of *Bifidobacterium Longum* object of the present invention are resistant so that they do not undergo remarkable mortality either during the technological processes of production of the pharmaceutical or alimentary preparations, or throughout the normal period of storing thereof. As a matter of fact these bacterial preparations have been submitted to stability tests that showed an extremely good resistance of the two bacterial strains at room temperature so that their sale can be continued for no less than two years after their manufacture.

The examples reported hereinafter are useful for a further illustration of the invention and have not to be considered as a limitation thereof.

EXAMPLE 1

Manufacturing Method of the Bacterial Culture of the *Bifidobacterium Longum* W11 Strain The "primary culture" of the strain of *Bifidobacterium Longum* W11 used as inoculation in the industrial fermentations is exactly the same as that deposited at the Belgian Coordinated Collections of Microorganisms—BCCM LMG-Collection—Laboratorium voor Microbiologie, Universiteit Gent, which on acceptance of the strain dispatched has ratified the purity and the vitality of the strain and has registered it with the accession number LMG P-21586.

In order to obtain this "primary culture", said strain has been grown in a culture medium called TPY having the following composition when referred to one liter:

| | |
|---|---|
| Tryptic peptone of casein | 10 g |
| Soy-bean peptone | 5 g |
| Yeast extract | 5 g |
| Glucose | 10 g |
| Anhydrous $K_2HPO_4$ | 2 g |
| $MgCl_2.6H_2O$ | 0.5 g |
| $ZnSO_4.7H_2O$ | 0.25 g |
| $CaCl_2.2H_2O$ | 0.15 g |
| Tween 80 | 1 ml |
| Cysteine hydrochloride | 0.5 g |
| Bidistilled water | qs to 1000 ml |

The growth has been carried out at 37° C. for 20 hours and then the culture has been shared, with the addition of suitable cryoprotectors selected from proteids, carbohydrates and mineral salts, in vials that have been freezed and stored in liquid nitrogen at −196° C.

Starting from the "primary culture", with a 3% inoculation percentage, 3 sub-cultures have been prepared with the aim to increase the number of cells of the bacterial strain.

The last sub-culture of about 10 liters, called "mother culture", has been used to inoculate the reactor of the "intermediate culture" having a capacity of about 300 liters.

The subsequent process of industrial manufacture of the biologically pure culture of *Bifidobacterium Longum* W11 comprises the following steps:

1. fermentation at a controlled pH between 6.5 and 7.0;
2. separation of the bacterial biomass from the culture broth;
3. protection of the bacterial biomass by means of a solution of cryoprotectors selected from proteids, carbohydrates and mineral salts with the aim to safeguard the cells' vitality during the subsequent steps of freezing and lyophilizing, and possibly also by including in a proteic precipitate with the aim of also giving a resistance of the strain to the enzymatic degradation and to conditions of acidic pH;
4. lyophilization;
5. milling and granulation of the lyophilized culture;
6. blending of the lyophilized culture;
7. packaging.

The obtained product contains about $8 \div 10 \times 10^{10}$ vital cells for each gram.

EXAMPLE 2

Manufacturing Method of the Bacterial Culture of the *Bifidobacterium Longum* W11a Strain The biologically pure bacterial culture of the *Bifidobacterium Longum* W11a has been prepared according to the method described in example 1 by starting from a "primary culture" of the strain of *Bifidobacterium Longum* corresponding exactly to that deposited at the Belgian Coordinated Collections of Microorganisms—BCCM LMG-Collection—Laboratorium voor Microbiologie, Universiteit Gent, which has ratified the purity and the vitality of the strain and has registered it with the accession number LMG P-21587.

EXAMPLE 3

Colonizing Tests in Vivo

The tests have been carried out on 4 groups of 2 mice, each mouse has received two doses, the second one 16 hours after the first one, of a glucose solution containing *Bifidobacterium Longum* LMG P-21586 at a concentration equal to $1.6 \times 10^9$ CFU/60 μl.

The capability of the strain in colonizing the intestine of these mice has been checked by calculating the amount of *Bifidobacterium Longum* present in the faeces: the first sampling has been carried out before starting the administrations, while the subsequent samplings have respectively been carried out 2, 4, 8, 24, 48 hours after the second administration. The amount of the strain of *Bifidobacterium Longum* found in the faeces has been in the region of $10^6$ CFU/g, so showing the occurred colonization. In particular it has been found that the *Bifidobacterium Longum* is resulted to be the main component of the bacterial flora with respect to all the strains of bifidobacteria found in the faeces.

EXAMPLE 4

Formulation in Bags in Association with Fructo-Oligosaccharides and Vitamins The preparation of bags each weighing 3 g to be dissolved in water or milk and containing 250 mg of biologically pure bacterial culture corresponding to about $2 \times 10^{10}$ alive cells of *Bifidobacterium Longum* W11, 2500 mg of fructo-oligosaccharides and vitamins of the B1, B2, B6 and B12 groups is reported as an example.

In particular, the product commercially available called Actilight® 950P made of a mixture of fructo-oligosaccharides formed by a chain of fructose molecules joined to one glucose molecule of general formula GFn with $n \leq 4$ and with a polymerization degree between 2 and 10 has been used as fructo-oligosaccharide.

The detailed quali-quantitative composition of the bags is as follows:

| Component | mg |
|---|---|
| Bifidobacterium Longum W11 | 250 |
| Actilight ® 950P | 2500 |
| Vitamin B1 | 1.4 |
| Vitamin B2 | 1.6 |
| Vitamin B6 | 2 |
| Vitamin B12 | 0.001 |
| Mandarin Aroma | 20 |
| Aspartame | 20 |
| Silica gel | 10 |
| Sorbitol | 195 |

Preparation Method

A first step of mixing of the vitamins with an aliquot part of Actilight® 950P is carried out followed by sifting on a sieve having 0.5 mm of net aperture. This first mixture is added with a second aliquot part of Actilight® 950P and a second mixing step is carried out. Lastly the bacterial culture of *Bifidobacterium Longum* W11, the remaining aliquot part of Actilight® 950P and the other components of the formulation are added with further mixing followed by an end sifting on a 0.8 mm sieve.

The product is then shared in aluminium bags weighing 3 g. The technological process of preparation of the bags does not cause any damage to the vitality of the strain.

Stability Tests

The stability tests have been carried out on the bags by measuring the bacterial charge at the time zero and respectively after 1, 2 and 3 months of storage at 22° C. so fixing the half-life time. The analysis of the data after 1, 2 and 3 months has shown how the mortality has been very low in these periods of time, so that it results that after two years the number of alive cells for each dose is no lower than $5 \times 10^9$ cells in the above said bag formulation. Said result shows how this preparation is fully adequate for the scopes the present invention wants to get.

EXAMPLE 5

Soft Gel Capsules Formulations in Association with Vitamins

Soft gel capsules with the following quali-quantitative composition:

| Component | mg |
|---|---|
| Bifidobacterium Longum W11 | 125 |
| Mono and diglycerides of the fatty acids | 14 |
| Soy-bean oil | 261.372 |
| Soy-bean lecithin | 5 |
| Natural tocopherols (E) | 16.418 |
| Thiamine mononitrate (B1) | 2.072 |
| Pyridoxine hydrochloride (B6) | 2.918 |
| Riboflavine (B2) | 1.920 |
| Cyanocobalamine 0.1% (B12) | 1.300 |
| Alimentary gelatine | 116 |
| Glycerol | 71 |
| Titanium dioxide | 4.140 |
| Yellow iron oxide | 0.200 | have been prepared by making a homogeneous suspension of the bacterial culture of *Bifidobacterium Longum* W11, of the vitamins, of the soy-bean lecithin and of the mono and diglycerides of the fatty acids in soy-bean oil, sharing said suspension in 7.5 oval size capsules made of alimentary gelatine, glycerol, titanium dioxide and yellow iron oxide and then by drying with an air flow at a temperature of about 21° C. and with about 20% moisture.

What is claimed is:

1. A biologically pure culture of a strain *Bifidobacterium Longum* LMG P-21586.

2. A biologically pure culture of a strain *Bifidobacterium Longum* LMG P-21587.

3. A pharmaceutical or alimentary preparation containing between $1 \times 10^7$ and $1 \times 10^{11}$ colony forming units of live cells of a biologically pure culture of a strain *Bifidobacterium Longum* LMG P-21586.

4. Preparation according to claim 3, comprising oligosaccharides.

5. Preparation according to claim 4, wherein the oligosaccharides are fructo-oligosaccharides with a polymerization degree between 2 and 10.

6. Preparation according to claim 3, comprising vitamins.

7. Preparation according to claim 6, wherein the vitamins are selecting from the group consisting of vitamins E, B1, B2, B6 and B12.

8. Preparation according to claim 3, in a form selected from the group consisting of capsules, tablets, packets, troches, liquid suspensions, dry oral supplements, liquid oral supplements, vials, milk, yogurt, fresh cheese, ice-creams, products made of fermented cereals, milk powders, children's products and products for domestic animals.

9. A pharmaceutical or alimentary preparation containing between $1 \times 10^7$ and $1 \times 10^{11}$ colony forming units of live cells of a biologically pure culture of a strain *Bifidobacterium Longum* LMG P-21587.

10. Preparation according to claim 9, comprising oligosaccharides.

11. Preparation according to claim 10, wherein the oligosacharides are fructo-oligosaccharides with a polymerization degree between 2 and 10.

12. Preparation according to claim 9, comprising vitamins.

13. Preparation according to claim 12, wherein the vitamins are selected from the group vitamins E, B1, B2, B6 and B12.

14. Preparation according to claim 9, in a form selected from the group consisting of capsules, tablets, packets, troches, liquid suspensions, dry oral supplements, liquid oral supplements, vials, milk, yogurt, fresh cheese, ice-creams, products made of fermented cereals, milk powders, children's products and products for domestic animals.

* * * * *